(12) United States Patent
Thurier et al.

(10) Patent No.: US 7,678,932 B2
(45) Date of Patent: Mar. 16, 2010

(54) PROCESS FOR CO-PRODUCING OLEFINS AND ESTERS BY ETHENOLYSIS OF UNSATURATED FATS IN NON-AQUEOUS IONIC LIQUIDS

(75) Inventors: Cyril Thurier, Rennes (FR); Helene Olivier-Bourbigou, Saint Genis Laval (FR); Pierre Dixneuf, Rennes (FR); Gerard Hillion, Herblay (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 1083 days.

(21) Appl. No.: 11/286,351

(22) Filed: Nov. 25, 2005

(65) Prior Publication Data

US 2006/0079704 A1 Apr. 13, 2006

(51) Int. Cl.
  *C07C 51/00* (2006.01)
(52) U.S. Cl. .................................. 554/124; 585/500
(58) Field of Classification Search .................. 554/124; 585/500
  See application file for complete search history.

(56) References Cited

U.S. PATENT DOCUMENTS

| 4,545,941 | A | 10/1985 | Rosenburg et al. |
| 5,475,159 | A | 12/1995 | Singleton et al. |
| 5,675,051 | A | 10/1997 | Chauvin et al. |
| 6,756,500 | B1 | 6/2004 | Guertler et al. |

FOREIGN PATENT DOCUMENTS

WO  WO 02076920 A1 * 10/2002

OTHER PUBLICATIONS

Warwel S. et al., "Polymers and surfactants on the basis of renewable resources," Chemosphere, Pergamon Press, Oxford, GB, vol. 43, 2001, pp. 39-48.
Database Caplus, Chemical Abstracts Service, Columbus, OH; Database accession No. 1984:432612; V.O. Polotnyuk et al., "Use of photoionization detector for identification of components of complex hydrocarbon mixtures." Zhurnal Analiticheskoi Khimii; vol. 39, No. 3, 1984, pp. 529-532.
Database Caplus, Chemical Abstracts Service, Columbus, OH; Database accession No. 1996:437700; A. Hefetz et al., "The exocrinology of the queen bumble bee Bombus terrestris," Zeitschrift fur Naturforschung, vol. 51, No. 5/6, 1996, pp. 409-422.
H. Olivier-Bourgigou et al., "Ionic-liquids: perspectives for organic and catalytic reactions." Journal of Molecular Catalysts, vol. 182-183, 2002, pp. 419-437.

* cited by examiner

*Primary Examiner*—Deborah D Carr
(74) *Attorney, Agent, or Firm*—Millen, White, Zelano, Branigan, P.C.

(57) ABSTRACT

A process is described in which an unsaturated fat is reacted with ethylene in a metathesis reaction in the presence of at least one non-aqueous ionic liquid to produce both an olefinic fraction and a composition of monoalcohol or polyol esters.

Particular application to an oleic sunflower seed oil, an oleic rapeseed oil or to a mixture of monoalcohol esters of said oils, the process producing both an olefinic fraction and a monoalcohol or glycerol esters composition generally having more than half of its chains constituted by unsaturated $C_{10}$ chains.

20 Claims, No Drawings

PROCESS FOR CO-PRODUCING OLEFINS AND ESTERS BY ETHENOLYSIS OF UNSATURATED FATS IN NON-AQUEOUS IONIC LIQUIDS

The invention relates to the co-production of olefins and esters by metathesis using ethylene (or ethenolysis) of unsaturated fats in the presence of a catalyst and at least one non-aqueous ionic liquid.

PRIOR ART

The olefin metathesis reaction is a reaction which is well known in organic chemistry. That reaction, which is carried out in the presence of a suitable catalytic system, consists of exchanging alkylidene groups between two olefins in accordance with the following equations:

1) The first case, "self metathesis" or "homometathesis" (i.e. metathesis of one molecule of olefin on another molecule of the same olefin):

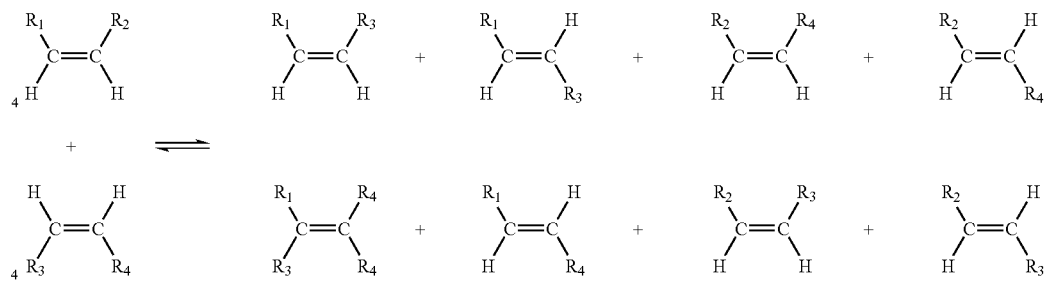

2) The second case, "cross metathesis" (i.e. metathesis between two different olefins):

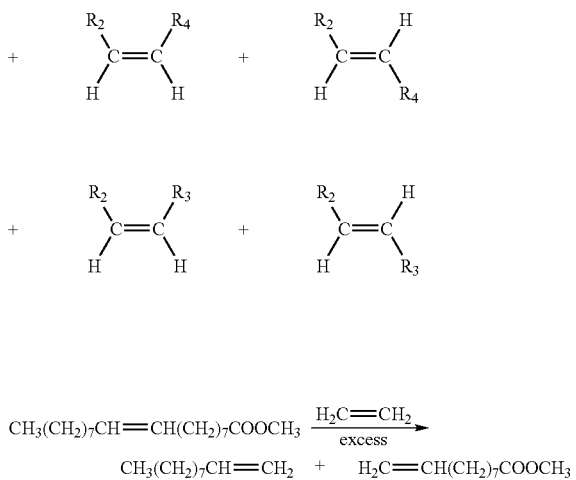

The olefin metathesis reaction is an equilibrated reaction. It may occur in the presence of a wide variety of catalysts, usually based on transition metals from groups IVA to VIII, including tungsten, molybdenum, rhenium and ruthenium, either in the homogeneous phase or in the heterogeneous phase. A number of reviews and scientific works deal with this aspect. Examples which may be cited are:

- K. J. Ivin and J. C. Mol in "Olefin metathesis and metathesis polymerization", San Diego, Academic Press (1997);
- "Handbook of metathesis", R. H. Grubbs (ed), Wiley-VCH, Weinheim (2003);
- J. C. Mol, "Industrial applications of olefin metathesis", J. Mol. Catal. 213, 39 (2004);
- D. Séméril and P. H. Dixneuf, in "Novel metathesis chemistry: Well defined initiator systems for specialty chemical synthesis, tailored polymers and advanced material applications", Y. Imamoglu and L. Bencze (Eds), Kluwer Academic Publishers, The Netherlands (2003), 1-21.

If one of the olefins is an unsaturated fatty acid ester represented, for example, by methyl oleate, the reaction leads to the production of one or more olefins and one or more unsaturated esters. The reaction can be written as follows:

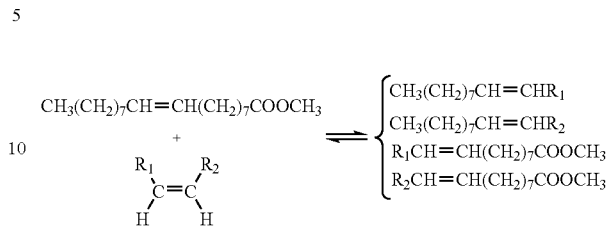

If the olefin $R^1HC=CH R^2$ is ethylene and it is used in a sufficient excess to displace the equilibrium, the reaction may result in an alpha-olefin and an unsaturated ester, in this particular case 1-decene and methyl 9-decenoate. The particular reaction may be written as follows:

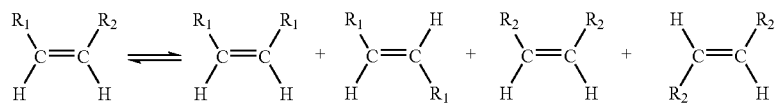

This reaction is of great potential interest as it allows the manufacture to be envisaged, from a starting material which is essentially of vegetable or animal origin (and is thus renewable) of products such as an alpha-olefin, in this particular case 1-decene, which is a desirable intermediate in petrochemistry, normally entirely manufactured from fossil starting materials such as ethylene.

This reaction of metathesis by ethenolysis applied to fatty acid esters has been reported in many publications and scientific reviews. Recent examples which can be cited are:

- "Application of olefin metathesis in oleochemistry: an example of green chemistry", J. C. Mol, Green Chemistry, 4, 5-13 (2002);

"The metathesis of polyunsaturated fatty esters using the homogeneous W(O-2,6-$C_6H_3X_2$)$_2$Cl$_4$/Me$_4$Sn catalytic systems", by B. B. Marvey et al, J. Mol. Catal. 213, 151-157 (2004);

"Technological and economical aspects of the metathesis of unsaturated esters" by M. Sibeijn et al, JAOCS, 71, 6 (1994);

"Polymer and surfactants on the basis of renewable resources", by S. Warwel et al, Chemosphere 43, 39-48 (2001);

"Catalysis metathesis of unsaturated fatty acid esters and oils", by J. C. Mol, Topics in Catalysis, 27, 1 (2004).

Various types of catalyst have been described for carrying out this transformation. The first systems were homogeneous, based on tungsten and tetraalkyl tins, for example WCl$_6$/SnMe$_4$. This was followed by heterogeneous systems based on rhenium activated by tetraalkyl tins. However, such systems have the disadvantage of using co-catalysts, generally based on tin which may contaminate the reaction products. More recently, homogeneous "well defined" systems using no co-catalyst and based on metal-carbenes (M=C) have been described, the metal being tungsten or molybdenum. However, the main difficulty encountered with all of these systems remains their poor compatibility with functional groups such as acids or esters, for example those present in vegetable oils. This generally means low activity and rapid deactivation of such catalytic systems.

Complexes based on ruthenium have rapidly proved themselves to be very interesting because of their tolerance of a wide range of functional groups. That property, coupled with an activity which is often high, explains their major development in the field of polymer synthesis and in organic synthesis.

Their use to catalyze the metathesis of vegetable oils has been studied widely. The following references can be provided:

International patent application WO-A-96/04289 (R. Grubbs et al) describes the ethenolysis of methyl oleate with complexes of type 1 (Figure 1 below). In the presence of excess ethylene (100 psi), the reaction produces a mixture of decenes (43%), methyl decenoate (46%) and, moreover, homometathesis products (5%).

International patent application WO-A-99/51344 (W. Herrmann et al), U.S. Pat. No. 6,635,768 (Herrmann et al) and US patent application US-A1-2004/0095792 (Herrmann et al) describe the use of complexes analogous to type 2 (Figure 1 below) to catalyze the homometathesis of methyl oleate and the metathesis of methyl oleate with 1-octene. The latter complexes may be more active but also show isomerizing activity of the double bond, which limits their selectivity for the production of alpha olefins.

International application WO-A-02/076920 (Newman et al) describes the use of type 3 ruthenium complexes (Figure 1 below) in a homogeneous medium or a medium supported on polymers, for example of the polystyrene type. The special feature of such complexes compared with those above is that they carry a chelated ligand. Clearly, immobilizing the complex on a solid support considerably reduces the activity of the system.

Type 1 complexes: L1 and L2 are phosphines

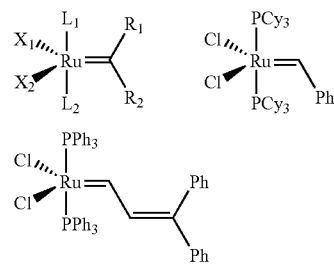

Example of Type 1 Complexes

Type 2 complexes: L1 or L2 is a heterocyclic carbene

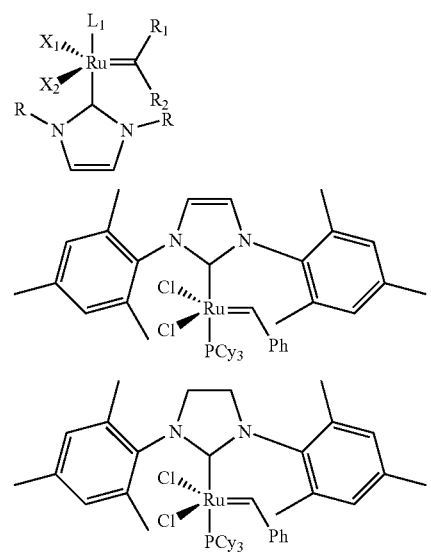

Examples of Type 2 Complexes

Type 3 Complexes

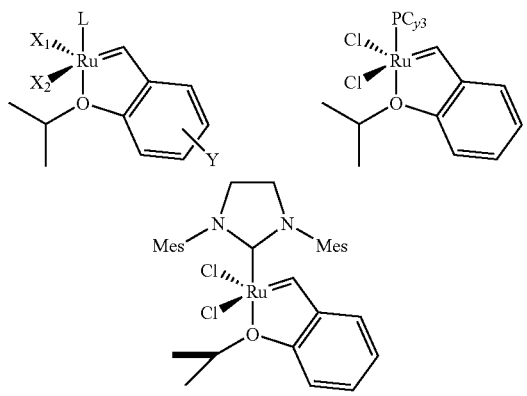

Examples of Type 3 Complexes

Figure 1

One of the principal difficulties of such systems based on ruthenium is their service life, which is too short. Using them in the homogeneous phase produces the most active complexes, but raises the problem of separating the reaction products and recycling them.

One interesting approach consists of immobilizing the catalyst in a liquid phase (solvent) from which the products can readily be separated either by distilling or by decanting if the products are only slightly miscible with the solvent.

Non-aqueous ionic liquids with general formula $Q^+A^-$ have been shown to be particularly advantageous solvents for this application. They have a very low vapour tension (do not distill) and physico-chemical properties which can be modified as a function of the anion and cation in them (see, for example, H. Olivier-Bourbigou, L. Magna, *J. Mol. Catal. A, Chem*, 2002, vol 182, p 419).

Immobilizing ruthenium based catalysts in ionic liquids has been described but little literature exists in this area. An example which may be cited is European patent EP-B-1 035 093. However, the described applications only concern cases of ring closing or ring opening metathesis (RCM or ROMP) and do not describe examples of cross metathesis.

The ethenolysis of unsaturated fats has not been described in ionic liquids. However, it has been shown (B. R. Maughon et al, Organometallics 23, 2027, 2004), that:
- firstly, the selectivity of the reaction for the terminal olefin (for example 1-decene) depends on the degree of conversion of the substrate (for example methyl oleate): the greater the conversion, the lower the selectivity;
- further, the loss of catalyst activity could be attributed in part to the presence and concentration of the terminal olefin in the medium.

The development of a process for the ethenolysis of unsaturated fats which is economically viable thus involves:
- developing a stable catalyst which is selective for ethenolysis (avoids homometathesis) and does not isomerize the double bond to a great extent;
- a process in which the alpha olefin co-produced during the reaction is selectively extracted from the reaction medium to prevent its inhibiting effect on the catalyst;
- a process in which the catalyst can be recycled and re-used.

The invention pertains to a process involving the metathesis of unsaturated fats with an excess of ethylene in the presence of a catalyst comprising at least one ruthenium compound and in the presence of at least one non-aqueous ionic liquid, for example.

More particularly, the invention concerns a process for the metathesis of fats selected from oleic sunflower oils, oleic rapeseed oils and monoalcohol esters of said oils.

In this novel process, the catalyst (for example based on a ruthenium complex) is immobilized and stabilized in the non-aqueous ionic liquid in which the olefins produced are only slightly miscible. These are thus extracted during the reaction, and as they are formed, into a second phase.

In this novel process, the reaction products may be separated readily from the ionic liquid containing the catalyst either by distillation, because of the non-volatility of the ionic liquid, or by decanting due to the low solubility of the olefins formed in the ionic liquid. The catalyst remains immobilized and stabilized in the ionic liquid. This latter containing the catalyst may be recycled and re-used.

This process is used to obtain particular compositions of products which are separated into distinct fractions each having a different use.

The Feed

The metathesis process of the invention is applicable to any fat comprising at least one ester formed between at least one monocarboxylic acid, for example containing at least 12 carbon atoms, comprising at least one ethylenically unsaturated bond and at least one hydroxylated saturated aliphatic compound (monoalcohol or polyol), the monoalcohol being, for example, a monoalcohol containing 1 to 8 carbon atoms, and a particular polyol being glycerol (case of unsaturated vegetable oils).

More particularly, the process of the invention may be applied to esters of oleic acid, a fatty acid the chain of which carries a single unsaturated bond. In this case, the ethenolysis reaction leads to the formation of only two products, 1-decene and an ester of 9-decenoic acid. However, natural fats of a vegetable or animal origin do not tend to exclusively contain fatty chains constituted by oleic chains. The production of an ester of pure oleic acid thus necessitates recourse to a separation and purification operation which usually employs distillation under tricky and therefore expensive conditions.

If one of the olefins is an ester of a di-unsaturated fatty acid such as the methyl ester of linoleic acid and the other olefin is ethylene used in sufficient excess, the metathesis reaction will result in the production of an olefin, 1-heptene, a di-olefin, 1,4-pentadiene, and an unsaturated ester, methyl 9-decenoate. The reaction may be written as follows:

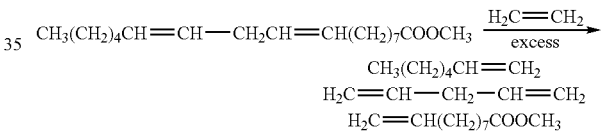

In this reaction, the metathesis reaction by ethenolysis is assumed to be complete, i.e. all of the unsaturated bonds of the linoleate chain have reacted with the ethylene used in excess. However, an incomplete metathesis reaction, i.e. involving just one of the two unsaturated bonds of the linoleate chain could result in the following products:

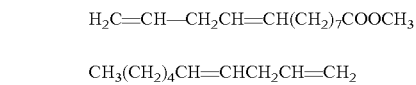

The same reactions can be applied to all of the unsaturated chains of known fatty acids, for example the chains of tri-unsaturated linolenic type acids. The number of possible products will be even larger as the number of unsaturated bonds carried by the chain increases.

The metathesis ethenolysis reaction may also be applicable not to an ester of an unsaturated fatty acid monoalcohol ester, but to the corresponding triglyceride. The reaction may, for example, be written as follows:

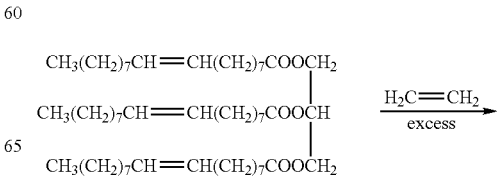

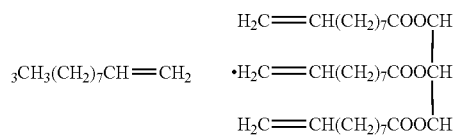 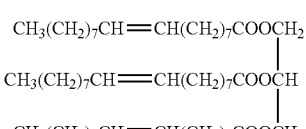

If this reaction of metathesis by ethenolysis is applied not to a single chain of fatty acid, for example oleic or linoleic acid as above, but to a mixture of said fatty acid chains, as is the case in reality when products are of vegetable or animal origin, a mixture of products derived from metathesis by ethenolysis of each of the fatty chains involved will be obtained.

The nature of the products obtained and their quantity will thus depend on the fatty acid composition (nature and abundance) of the fatty starting material used.

Obtaining products which are rich in 1-decene implies using a starting material which is rich in oleic acid esters.

The vegetable oil under consideration (or the monoalcohol ester of said oil) is selected from oleic sunflower seed oil or oleic rapeseed oil (or monoalcohol esters of said oils). These particular oils and monoalcohol ester derivatives of said oils are characterized by their fatty acid composition, in particular by the nature and proportion of their unsaturated fatty acids. In these oils or monoalcohol esters of said oils, in general at least 80% of the fatty acid chains are constituted by oleic chains, the amount of linoleic fatty chains does not exceed 12% and the amount of linolenic fatty chains does not exceed 0.3%. No other olefinic chain is present in said oils or in monoalcohol esters of said oils in an amount of more than 0.3% while the amount of saturated chains, for example palmitic or stearic, is in the range 5% to 15%.

Said oils may be used in their natural triglyceride form or in the form of a mixture of monoalcohol esters, for example methanol, ethanol, propanol, or, more generally, any monoalcohol containing 1 to 8 carbon atoms.

The reactions and the products formed are as follows:
in the case of an ester of a monoalcohol represented by methanol, for example, with an oleic sunflower or oleic rapeseed oil:

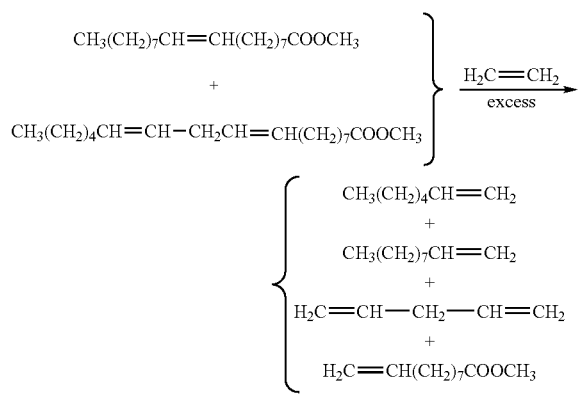

in the case of an oleic sunflower or oleic rapeseed oil:

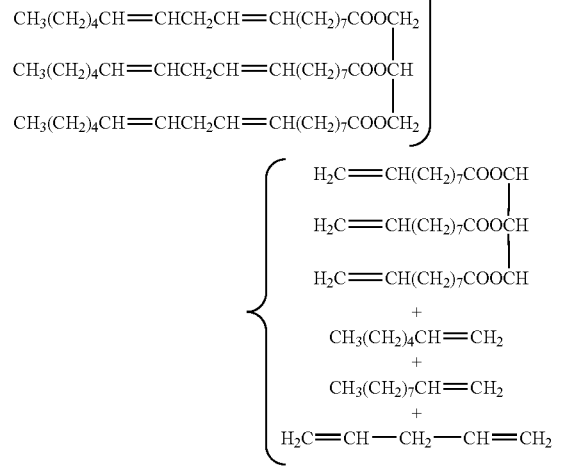

In all cases, the saturated fatty acid esters present in the oleic sunflower oil or oleic rapeseed oil or in monoalcohol esters of said oils are not reactive in metathesis reactions and are recovered at the end of the operation. Thus, they do not figure in the equations.

In all cases, when the metathesis reaction is complete, the products obtained can be classified into four families:
  mono-olefins of the alpha-olefin type: 1-decene and 1-heptene;
  a diolefin, 1,4-pentadiene;
  unsaturated esters whether in the form of a monoalcohol 9-decenoate or in the form of 9-decenoic acid triglyceride;
  saturated esters present in the starting material and which are not involved in the metathesis reaction.

If the metathesis reaction is not complete, these products are supplemented by residual esters of oleic acids and linoleic acid in the form of monoalcohol esters or in the form of triglycerides.

The process of the present invention may comprise a step for separating olefins by evaporation. In fact, mono-olefins (1-decene and 1-heptene) and diolefin (1,4-pentadiene) can readily be separated from the reaction medium by evaporation, their respective boiling points being 166.5° C., 94° C. and 26° C., thus much lower than that of the esters present and formed.

In the process of the present invention, the mixture of olefins isolated previously may undergo distillation aimed at separating 1,4-pentadiene, 1-heptene and 1-decene, as well as all excess ethylene.

The excess ethylene may be re-used during a new metathesis reaction, while each of the other mono (or di-) olefins may be upgraded and used separately.

After evaporating off the purely olefinic fraction (mono- and diolefins), the residual reaction medium consequently contains a mixture of esters, i.e. an ester of 9-decenoic acid ester in the form of a monoalcohol ester or in the form of a glycerol tri-ester, depending on the starting material used (oil or monoalcohol ester of said oil), and also esters of saturated acids present in the starting material, i.e. esters of palmitic and stearic acids in the monoalcohol ester form or in the form of glycerol tri-esters depending on the starting material used. Said saturated structures are not involved in the metathesis reaction.

Said ester fraction may be defined by its composition, which derives from the composition of the oil or the mixture of monoalcohol esters of the starting oil.

Starting from an oil as defined above (oleic sunflower oil or oleic rapeseed oil) or a mixture of monoalcohol esters of one of said oils, the composition of mono and diolefins could be as indicated above.

Then, by metathesis of the oleic sunflower oil or the oleic rapeseed oil or their monoalcohol esters with a particular olefin such as ethylene used in excess, it is possible to obtain in isolation:
 firstly, an olefinic fraction primarily (i.e. at least 80%) comprising 1-decene, as well as 1-heptene and 1,4-pentadiene;
 and a composition of monoalcohol or glycerol esters rich in $C_{10}$ unsaturated acid ester.

Starting from an oil more than 80% of the fatty chains of which are constituted by oleic acid or a mixture of monoalcohol esters of said oil, a metathesis reaction by ethenolysis will produce the following, if the yield of said reaction is at least 80%:
 firstly, a principal olefinic fraction of 1-decene;
 and secondly, after eliminating mono- and diolefins by evaporation, a mixture of esters more than half of the chains of which will be constituted by $C_{10}$ unsaturated chains. Such a composition does not correspond to any known fat.

Said mixture of esters is characterized in that its concentration of $C_{10}$ unsaturated chains is very high. It is also characterized by the position of the unsaturated bond located between the carbon atom in the 9 position and that in position 10 on the carbon chain. This position of the unsaturated bond is different from that observed in the natural products.

Consider, for example, a methyl ester of an oleic sunflower seed oil the composition of which is as follows:
 methyl oleate: about 83% by weight;
 methyl linoleate: about 10% by weight;
 methyl palmitate: about 3% by weight;
 methyl stearate: about 4% by weight.

When the metathesis reaction is complete—i.e. when each unsaturated bond carried by the fatty chains has reacted with one mole of ethylene as shown in the reaction scheme described above—, a mixture having the following composition is obtained:
 1-decene: about 35.8% by weight;
 1-heptene: about 3.0% by weight;
 1,4-pentadiene: about 2.1% by weight;
 methyl 9-decenoate: about 52.7% by weight;
 methyl palmitate: about 2.75% by weight;
 methyl stearate: about 3.65% by weight.

An evaporation operation at a temperature of less than 180° C. can isolate an olefinic cut having the following composition:
 1-decene: about 87.5% by weight;
 1-heptene: about 7.3% by weight;
 1,4-pentadiene: about 5.1% by weight.

These compounds could be separated by distillation in a subsequent step using known methods.

The non-evaporated ester fraction will have the following composition:
 methyl 9-decenoate: about 89.2% by weight;
 methyl palmitate: about 4.6% by weight;
 methyl stearate: about 6.2% by weight.

Said ester fraction has a completely novel composition. No known fat has said composition.

If the starting material used is an oleic sunflower oil in its triglyceride form, the olefinic fraction will be comparable and the esters obtained will be of the triglyceride type instead of being in the form of the methyl ester. In this case, for the same reaction yield, the fatty acid compositions will be very slightly different.

In the case of a mixture of esters of a monoalcohol other than methanol, the weight ratio between the olefinic and ester fractions will depend on the molar mass of the monoalcohol under consideration; however, the mole ratio between the products obtained will remain identical, as it only depends on the reaction yield.

Subsequent total or partial hydrogenation of the unsaturated bonds of the mixture will lead to a mixture of esters the composition of which is comparable to that of coprah or palm nut oils or their ester derivatives in the sense that the majority of the chains are saturated and carry fewer than 12 carbon atoms. The known and possible applications of said oils—the culture of which is not carried out on a large scale in Europe—or of their derivatives may be envisaged for the ester fractions derived from the metathesis of oils of the invention or their monoalcohol esters. Said applications primarily concern the manufacture of soaps by saponification, the manufacture of fatty acids by hydrolysis, etc.

1-decene is a highly desirable synthesis intermediate. It is involved in the manufacture of poly alpha olefins, which are synthesis lubricants, as well as in the preparation of alcohols and in many other industrial scale manufacturing processes. 1-decene is generally prepared by oligomerization of ethylene, i.e. entirely from a starting material of fossil origin.

1-heptene and 1,4-pentadiene are synthesis intermediates generally derived from cracking petroleum or coal cuts.

Using the process of the invention, said compounds are thus accessible, no longer only from the fossil starting material, but primarily from renewable starting materials derived from biomass, such as oleic sunflower seed oil or oleic rapeseed oil. As an example, one mole of 1-decene may be obtained from one fatty acid chain and half a mole of ethylene. 5 moles of ethylene are required to prepare 1 mole of 1-decene solely from ethylene by oligomerization thereof.

The Ionic Liquid

The non-aqueous ionic solvent is selected from the group formed by liquid salts which have general formula $Q^+A^-$ in which $Q^+$ represents a quaternary ammonium and/or a quaternary phosphonium and $A^-$ represents any anion which can form a liquid salt at low temperatures, i.e. below 90° C., advantageously at most 85° C., and preferably less than 50° C.

The anions $A^-$ are preferably selected from halides, nitrate, sulphate, alkylsulphates, phosphate, alkylphosphates, acetate, halogenoacetates, tetrafluoroborate, tetrachloroborate, hexafluorophosphate, trifluoro-tris-(pentafluoroethyl) phosphate, hexafluoroantimonate, fluorosulphonate, alkylsulphonates (for example methylsulphonate), perfluoroalkylsulphonates (for example trifluoromethylsulphonate), bis(perfluoroalkylsulphonyl)amides (for example bis-trifluoromethylsulphonyl amide with formula $N(CF_3SO_2)_2^-$), tris-trifluoromethylsulphonyl methylide with formula $C(CF_3SO_2)_3^-$, bis-trifluoromethylsulphonyl methylide with formula $HC(CF_3SO_2)_3^-$, arenesulphonates, optionally substituted with halogens or halogenalkyl groups, the tetraphenylborate anion and tetraphenylborate anions the aromatic rings of which are substituted, tetra-(trifluoro acetoxy)-borate, bis-(oxalato)-borate, dicyanamide, tricyanomethylide, and the tetrachloroaluminate anion, or chlorozincate anions.

Cations $Q^+$ are preferably selected from the group formed by quaternary phosphonium, quaternary ammonium, quaternary guanidinium and quaternary sulphonium.

In the formulae below, $R^1$, $R^2$, $R^3$, $R^4$, $R^5$ and $R^6$ represent hydrogen (with the exception of the $NH_4^+$ cation for $NR^1R^2R^3R^4$), preferably a single substituent representing hydrogen, or hydrocarbyl radicals containing 1 to 30 carbon atoms, for example alkyl groups, saturated or unsaturated, cycloalkyls or aromatics, aryls or aralkyls, which may be substituted, containing 1 to 30 carbon atoms.

$R^1$, $R^2$, $R^3$, $R^4$, $R^5$ and $R^6$ may also represent hydrocarbyl radicals carrying one or more functions selected from the following: —CO$_2$R, —C(O)R, —OR, —C(O)NRR', —C(O)N(R)NR'R'', —NR'R'', —SR, —S(O)R, —S(O)$_2$R, —SO$_3$R, —CN, —N(R)P(O)R'R', —PRR', —P(O)RR', —P(OR)(OR'), —P(O)(OR)(OR') in which R, R' and R'', which may be identical or different, each represent hydrogen or hydrocarbyl radicals containing 1 to 30 carbon atoms.

The quaternary ammonium and/or phosphonium cations $Q^+$ preferably have one of general formulae $NR^1R^2R^3R^{4+}$ and $PR^1R^2R^3R^{4+}$ or one of general formulae $R^1R^2N=CR^3R^{4+}$ and $R^1R^2P=CR^3R^{4+}$ in which $R^1$, $R^2$, $R^3$ and $R^4$, which may be identical or different, are as defined above.

The ammonium and/or phosphonium cations may also be derived from nitrogen-containing and/or phosphorus-containing heterocycles comprising 1, 2 or 3 nitrogen and/or phosphorus atoms, with general formulae:

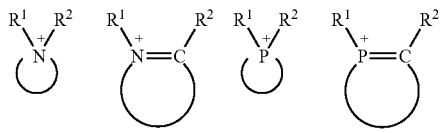

in which the cycles are constituted by 4 to 10 atoms, preferably 5 to 6 atoms, $R^1$ and $R^2$, which may be identical or different, being as defined above.

The quaternary ammonium or phosphonium cation may also have one of the following formulae:

$R^1R^{2+}N=CR^3—R^7—R^3C=N^+R^1R^2$ and $R^1R^{2+}P=CR^3—R^7—R^3C=P^+R^1R^2$ in which $R^1$, $R^2$ and $R^3$, which may be identical or different, are defined as above and $R^7$ represents an alkylene or phenylene radical.

Particular groups $R^1$, $R^2$, $R^3$ and $R^4$ which may be mentioned are methyl, ethyl, propyl, isopropyl, primary butyl, secondary butyl, tertiary butyl, amyl, phenyl or benzyl radicals; $R^7$ may be a methylene, ethylene, propylene or phenylene group.

Preferably, the ammonium and/or phosphonium cation $Q^+$ is selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, the 1-(2-hydroxyethyl)-3-methylimidazolium cation, the 1-(2-carboxyethyl)-3-methylimidazolium cation, diethylpyrazolium, N-butyl-N-methylpyrrolidinium, N-butyl-N-methylmorpholinium, trimethylphenylammonium, tetrabutylphosphonium and tributyl-tetradecylphosphonium.

The quaternary sulphonium and quaternary guanidinium cations preferably have one of the following general formulae:

$SR^1R^2R^{3+}$ and $C(NR^1R^2)(NR^3R^4)(NR^5R^6)^+$ in which $R^1$, $R^2$, $R^3$, $R^4$, $R^5$ and $R^6$, which may be identical or different, are as defined above.

Examples of salts which may be used in the invention that can be cited are 3-butyl-1-methylimidazolium bis(trifluoromethylsulphonyl)amide, 3-butyl-1,2-dimethylimidazolium bis(trifluoromethylsulphonyl)amide, N-butyl-N-methylpyrrolidinium bis(trifluoromethylsulphonyl)amide, 3-butyl-1-methylimidazolium tetrafluoroborate, 3-butyl-1,2-dimethylimidazolium tetrafluoroborate, 3-ethyl-1-methylimidazolium tetrafluoroborate, 3-butyl-1-methylimidazolium hexafluoroantimonate, 3-butyl-1-methylimidazolium trifluoroacetate, 3-ethyl-1-methylimidazolium triflate, 1-(2-hydroxyethyl)-3-methylimidazolium bis(trifluoromethylsulphonyl)amide, 1-(2-carboxyethyl)-3-methylimidazolium bis(trifluoromethylsulphonyl)amide, and N-butyl-N-methylmorpholinium bis(trifluoromethylsulphonyl)amide. These salts may be used alone or as a mixture.

The Catalysts

The catalysts used in the process of the invention to carry out the metathesis of unsaturated fats with excess ethylene may consist of any known metathesis catalyst, in particular catalysts comprising at least one ruthenium compound.

The ruthenium catalysts are preferably selected from charged or uncharged catalysts with general formula:

$(X_1)_a(X_2)_b Ru(carbene\ C)(L_1)_c(L_2)_d$ in which:
  a, b, c, d are whole numbers in which a and b equal 0, 1 or 2; c and d equal 0, 1, 2, 3 or 4;
  $X_1$ and $X_2$, which may be identical or different, each represent a mono- or multi-chelating ligand, charged or uncharged; examples which may be cited are halides, sulphate, carbonate, carboxylates, alcoholates, phenates, amides, tosylate, hexafluorophosphate, tetrafluoroborate, bis-triflylamide, tetraphenylborate and derivatives; $X_1$ or $X_2$ may be bonded to $Y_1$ or $Y_2$ or to (C carbene) to form a bidentate (or chelated) ligand on the ruthenium; and
  $L_1$ and $L_2$, which may be identical or different, are electron-donating ligands such as a phosphine, phosphite, phosphonite, phosphinite, arsine, stilbine, an olefin or an aromatic, a carbonyl compound, an ether, an alcohol, an amine, a pyridine or a derivative thereof, an imine, a thioether or a heterocyclic carbene which, for example, has one of the general formulae of Figure 2, in which $R_1$, $R_2$, $R_3$, $R_4$ and $R_5$, which may be identical or different, each represent hydrogen or a saturated or unsaturated or aromatic aliphatic hydrocarbon group containing 1 to 12 carbon atoms.

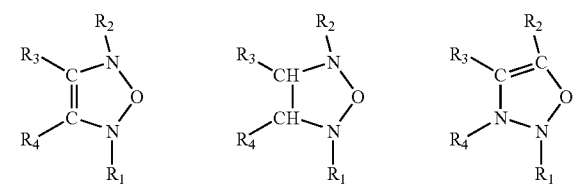

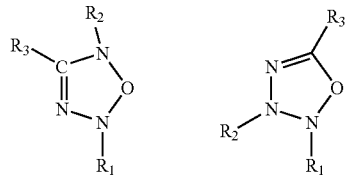

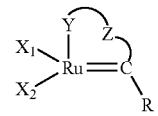

Figure 3

The "carbene C" may be represented by the general formula: $C(R_1)(R_2)$ in which $R_1$ and $R_2$ are identical or different, such as hydrogen or any other saturated or unsaturated, cyclic, linear or branched or aromatic hydrocarbonyl group. Examples which may be cited are alkylidene ruthenium complexes or cumulene complexes such as vinylidenes Ru=C=CHR, allenylidenes Ru=C=C=$CR_1R_2$, or indenylidenes.

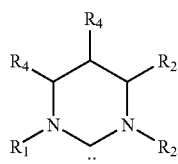

Figure 2

$L_1$ or $L_2$ may be bonded to the "carbene C" to form a bidentate or chelated ligand as indicated in the formula (Figure 3), in which Z represents a saturated, unsaturated or aromatic, cyclic or non cyclic aliphatic hydrocarbon bi-radical containing 1 to 12 carbon atoms; Y is a heteroelement such as oxygen, nitrogen, sulphur or phosphorus.

A functional group which can improve retention of the ruthenium complex in the ionic liquid may be grafted onto at least one of the ligands $X_1$, $X_2$, $L_1$, $L_2$ or onto the carbene C. This functional group may or may not be charged, and is preferably an ester, an ether, a thiol, an acid, an alcohol, an amine, a nitrogen-containing heterocycle, a sulphonate, a carboxylate, a quaternary ammonium, a guanidinium, a quaternary phosphonium, a pyridinium, an imidazolium, a morpholinium or a sulphonium.

Examples of functionalized complexes: possible position of function:

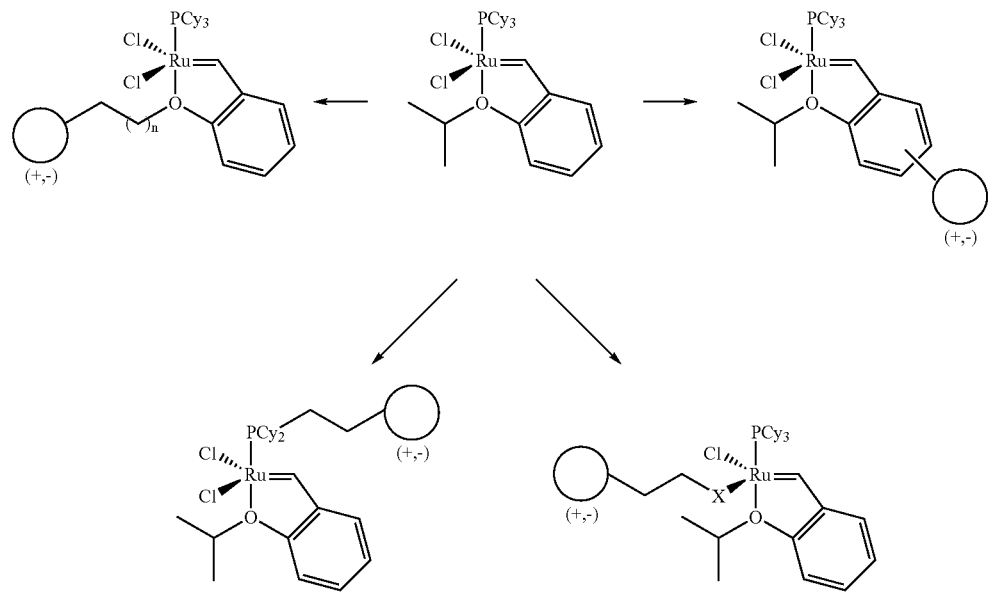

Of these ruthenium derivatives, the following examples may be cited:
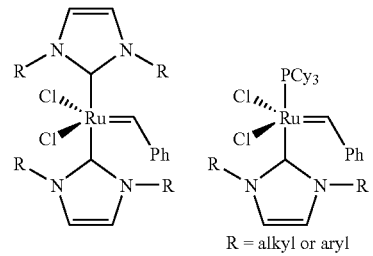
R = alkyl or aryl
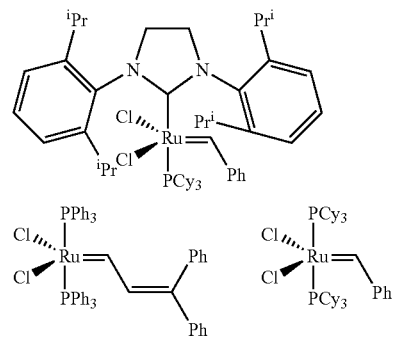
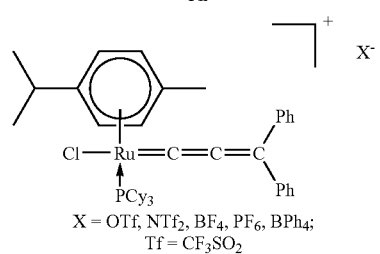
X = OTf, NTf$_2$, BF$_4$, PF$_6$, BPh$_4$;
Tf = CF$_3$SO$_2$
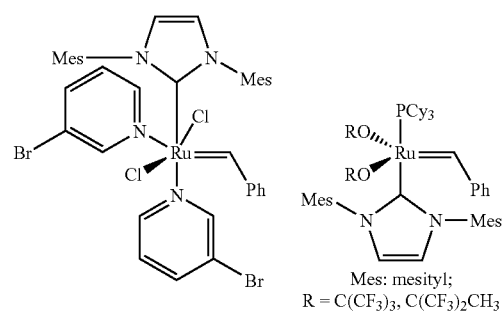
Mes: mesityl;
R = C(CF$_3$)$_3$, C(CF$_3$)$_2$CH$_3$
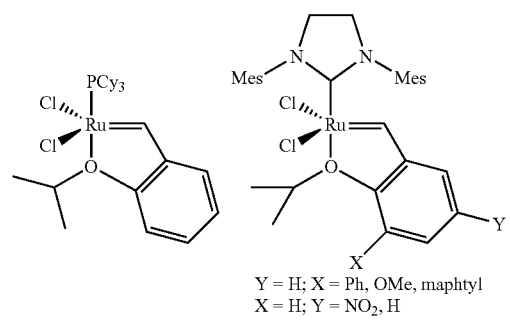
Y = H; X = Ph, OMe, maphtyl
X = H; Y = NO$_2$, H
-continued
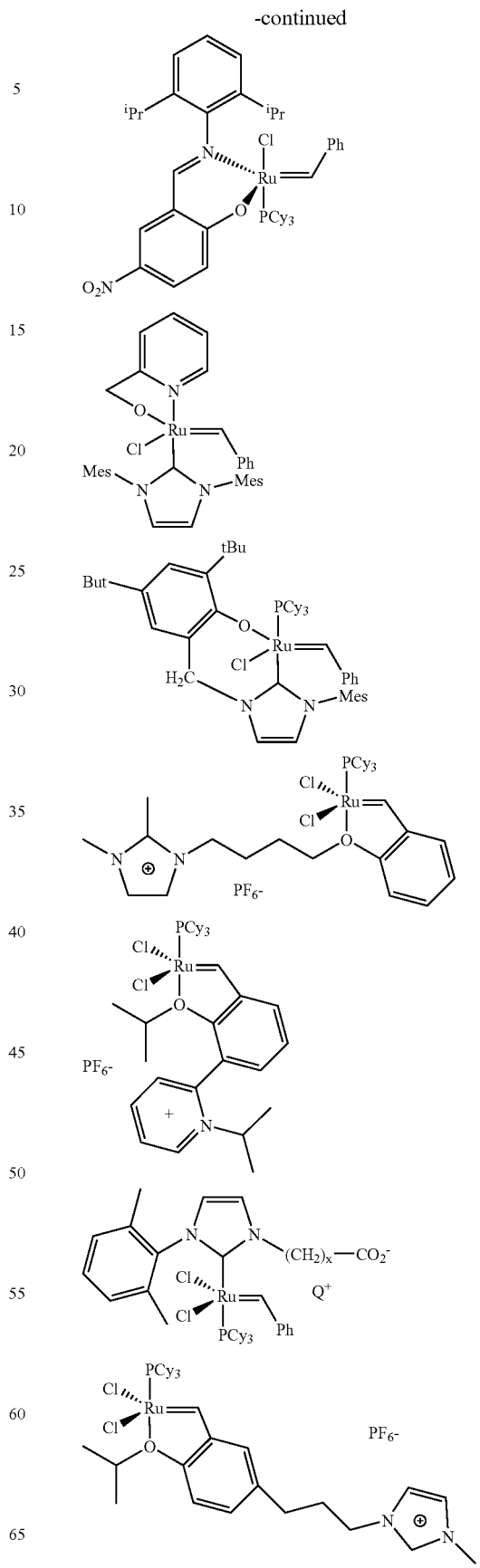

-continued

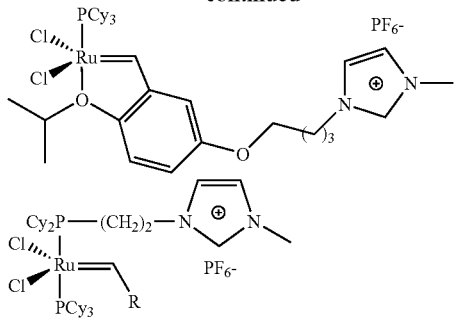

In these formulae, Cy represents the cyclohexyl radical and iPr represents the isopropyl radical. $Q^+$ represents an organic cation (for example ammonium, pyridinium, imidazolium or phosphonium), or an inorganic cation (for example Na+, Li+ or K+).

Implementation

In the process of the invention, in general the catalyst is introduced in proportions comprised between 0.001% molar and 10% molar with respect to the unsaturated starting fat. Preferentially, the content of catalyst is comprised between 0.01% and 10% molar.

In the process of the invention, metathesis of the starting fat (for example oleic sunflower oil or oleic rapeseed oil or their monoalcohol esters) with excess ethylene may be carried out in the absence or presence of an organic co-solvent. In the case in which a solvent or a mixture of solvents is used, its role may be to improve the solubility of the reagents and catalyst into the ionic liquid. It may also act to optimize extraction of the products in a second phase.

Examples of suitable solvents which may be cited are chloroalkanes, such as dichloromethane, chloroform or dichloro- or trichloro-ethane, aromatic solvents such as toluene, xylenes or chlorobenzene, or aliphatic solvents such as heptane or cyclohexane.

Metathesis of oleic sunflower oil or oleic rapeseed oil or their monoalcohol esters with ethylene used in excess may be carried out in a closed (batch) system, a semi-open system or a continuous system with one or more reaction steps. It is also possible to envisage carrying out the reaction using reactive distillation.

Vigorous agitation ensures good contact between the reagents (gas and liquid) and the catalytic mixture. The reaction temperature may be in the range 0° C. to +150° C., preferably in the range 20° C. to 120° C.

The operation may be carried out above or below the melting temperature of the medium, the dispersed solid state not being a limitation on the reaction.

The pressure may, for example, be in the range from atmospheric pressure to 50 MPa.

The ethylene may be used pure or as a mixture, or diluted with a paraffin (inert).

The reaction products may be separated by decanting.

It is also possible to separate the products by distillation if the ionic liquid is sufficiently non volatile and thermally stable.

The following examples illustrate the invention without limiting its scope.

EXAMPLE 1

Metathesis by Ethenolysis of Methyl Oleate Catalyzed by a Type 3 Complex (Figure 1) in an Ionic Liquid 1 ml of 3-butyl-1,2-dimethylimidazolium bis-triflylamide with formula $[BMMI]^+[N(CF_3SO_2)_2]^-$ pre-dried overnight at 80° C., 148 mg of methyl oleate (source: Fluka, with a purity higher than 98%) and 15 mg of the complex with formula $Cl_2Ru(=CH\text{-}o\text{-}O\text{-}iPrC_6H_4)PCy_3$ (synthesized by reacting the $1^{st}$ generation Grubbs complex with formula $Cl_2Ru(=CHC_6H_5)(PCy_3)_2$ with 1-isopropoxy-2-vinylbenzene in the presence of CuCl), this corresponding to 5% molar of catalyst with respect to methyl oleate, were introduced, in an inert atmosphere of argon, into an autoclave reactor provided with an agitation system and a pressure sensor. The autoclave was then placed under vacuum and pressurized to obtain a pressure of 10 bars (1 MPa) of ethylene (origin: Alphagas, quality N25). The temperature was kept constant at 20° C.

The medium was stirred at ambient temperature for 2 hours, then the excess ethylene was slowly purged by returning to atmosphere pressure at a temperature not exceeding 20° C. and the autoclave was again placed under an atmosphere of argon. The products were separated from the ionic liquid by adding 2 to 3 ml of heptane distilled over $CaH_2$ and degassed. An aliquot (100 µl) of the extracted solution was passed through a short silica column (2 cm) eluted with diethyl ether. It was analyzed by gas phase chromatography (ZB-1 column, 100% dimethylpolysiloxane, 30 metres, helium vector gas 2 ml/min, temperature programming: 60° C. then 5° C./min to 220° C.) coupled to a mass spectrometer.

The methyl oleate conversion was 95%. It was calculated using decane as an internal reference. The reaction products were composed of 1-decene and methyl decenoate.

The presence of 1-decene isomers was not detected. Homo-metathesis products were present in trace amounts and could not be quantified.

EXAMPLE 2

Recycling Ionic Liquid Containing Catalyst

After the first cycle carried out in accordance with Example 1, the autoclave containing the ionic liquid and the catalyst was placed under vacuum to eliminate traces of heptane. In an argon atmosphere, 148 mg of methyl oleate was added then the reactor was pressurized to obtain a pressure of 10 bars (1 MPa) of ethylene. The temperature was kept at 20° C.

The same procedure as that described in Example 1 was carried out to analyze the products formed.

3 successive cycles were carried out without adding catalyst or ionic liquid.

The methyl oleate conversion and the composition of the products formed were determined for each cycle (Table 1 below).

TABLE 1

| | Methyl oleate conversion (wt %) | Products formed |
|---|---|---|
| 1st cycle (Example 1) | 95 | 1-decene + methyl decanoate |
| 2nd cycle | 95 | 1-decene + methyl decanoate |
| 3rd cycle | 85 | 1-decene + methyl decanoate |

EXAMPLE 3

Metathesis by Ethenolysis of Methyl Oleate Catalysed by a Type 3 Complex (Figure 1) in a Ionic Liquid A 50 ml autoclave reactor was heated at 50° C. under dynamic vacuum (0.2 hPa) during 4 hours. After the temperature decreased to room temperature, 10 bar (1 MPa) of ethylene were introduced into the reactor. After a degassing made at the beginning of the test, 5 ml (7 g) of ionic liquid 1-butyl-1-methyl-pyrrolidinium bis(trifluoromethanesulfonyl)-amide with formula [BMPyrr][NTf$_2$] with a solution of 1 g (3.37 mmol) of methyl oleate and 80 mg of octadecane (used as internal standard for chromatography) were introduced into 10 ml of heptane. A solution of 49 mg (0.082 mmol) of the complex with formula:

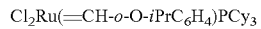

Cl$_2$Ru(=CH-o-O-iPrC$_6$H$_4$)PCy$_3$ was then added (this complex was synthesized by reacting the first generation Grubbs complex with formula Cl$_2$Ru(=CHC$_6$H$_5$)(PCy$_3$)$_2$ with 1-isopropoxy-2-vinylbenzene in the presence of CuCl) into 3 ml of toluene, this corresponding to 2.4% molar of catalyst with respect to the methyl oleate. The reactor was placed under 10 bar of ethylene pressure (1 MPa) during 2 h 15 and the temperature was kept constant at 25° C. The active medium was stirred with a magnetic bar (750 tr/min).

At the end of the reaction, the reactor was degassed and its content was completely taken in a glass syringe. The ionic liquid phase, more dense, was immediately reinjected into the reactor (under atmospheric ethylene pressure) and the organic phase, after filtration on a silica column eluted with toluene was analysed by gas chromatography.

The methyle oleate conversion was 95%. The reaction products were composed of 1-decene (yield 79%) and methyle decenoate (yield 72%).

Some traces of isomerization products (<1%) were detected. No self-metathesis products were observed.

EXAMPLE 4

Recycling of Ionic Liquid Containing the Catalyst

To the liquid phase obtained from the first cycle in Example 3, a solution of 1 g of methyle oleate and 80 mg of octodecane was added to 10 ml of heptane. The reactor was placed again under a 10 bar of ethylene pressure (1 MPa) during 2 h 15 and the temperature was kept constant at 25° C.

At the end of the reaction, the content of the reactor was treated in the same way as in Example 3.

After the second cycle, the methyle oleate conversion was 61%. The reaction products were composed of 1-decene (yield 57%) and methyle decenoate (yield 58%).

Some traces of isomerization products (<1%) were detected. No self-metathesis products were observed.

The invention claimed is:

1. A process for producing both an olefinic fraction and an ester composition, comprising contacting at least one unsaturated fat comprising at least one ester formed between at least one monocarboxylic acid comprising at least one ethylenically unsaturated bond and at least one aliphatic monoalcohol or at least one aliphatic polyol, under metathesis conditions, with an excess of ethylene in the presence of a catalyst and in the presence of at least one non-aqueous ionic liquid.

2. A process according to claim 1, wherein the non-aqueous ionic liquid is s liquid salts with general formula Q$^+$A$^-$ in which Q$^+$ represents a quaternary phosphonium, a quaternary ammonium, a quaternary guanidinium or a quaternary sulphonium and A$^-$ represents any anion which is capable of forming a liquid salt below 90° C.

3. A process according to claim 2, wherein the cations Q$^+$ have one of the following formulae: NR$^1$R$^2$R$^3$R$^{4+}$, PR$^1$R$^2$R$^3$R$^{4+}$, R$^1$R$^2$N=CR$^3$R$^{4+}$ or R$^1$R$^2$P=CR$^3$R$^{4+}$ in which R$^1$, R$^2$, R$^3$ and R$^4$, which may be identical or different, represent hydrogen with the exception of the cation NH$_4^+$ for NR$^1$R$^2$R$^3$R$^{4+}$, hydrocarbyl radicals containing 1 to 30 carbon atoms or hydrocarbyl radicals carrying one or more —CO$_2$R, —C(O)R, —OR, —C(O)NRR', —C(O)N(R)NR'R", —NR'R", —SR, —S(O)R, —S(O)$_2$R, —SO$_3$R, —CN, —N(R)P(O)R'R', —PRR', —P(O)RR', —P(OR)(OR'), —P(O)(OR)(OR') groups in which R, R' and R", which may be identical or different, each represent hydrogen or hydrocarbyl radicals containing 1 to 30 carbon atoms.

4. A process according to claim 2, wherein the quaternary ammonium and/or phosphonium cations are derived from nitrogen-containing and/or phosphorus-containing heterocycles comprising 1, 2 or 3 nitrogen and/or phosphorus atoms, with the formulae:

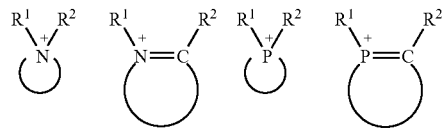

in which the cycles have 4 to 10 atoms and R$^1$ and R$^2$, which may be identical or different, are H, hydrocarbyl radicals containing 1 to 30 carbon atoms or hydrocarbyl radicals carrying one or more —CO$_2$R, —C(O)R, —OR, —C(O)NRR', —C(O)N(R)NR'R", —NR'R", —SR, —S(O)R, —S(O)$_2$R, —SO$_3$R, —CN, —N(R)P(O)R'R', —PRR', —P(O)RR', —P(OR)(OR'), —P(O)(OR)(OR') groups in which R, R' and R", which may be identical or different, each represent hydrogen or hydrocarbyl radicals containing 1 to 30 carbon atoms.

5. A process according to claim 2, wherein the quaternary ammonium or phosphonium cation has one of the following formulae:

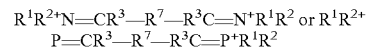

R$^1$R$^{2+}$N=CR$^3$—R$^7$—R$^3$C=N$^+$R$^1$R$^2$ or R$^1$R$^{2+}$P=CR$^3$—R$^7$—R$^3$C=P$^+$R$^1$R$^2$ in which R$^1$, R$^2$ and R$^3$, which may be identical or different, are H, hydrocarbyl radicals containing 1 to 30 carbon atoms or hydrocarbyl radicals carrying one or more —CO$_2$R, —C(O)R, —OR, —C(O)NRR', —C(O)N(R)NR'R", —NR'R", —SR, —S(O)R, —S(O)$_2$R, —SO$_3$R, —CN, —N(R)P(O)R'R', —PRR', —P(O)RR', —P(OR)(OR'), —P(O)(OR)(OR') groups in which R, R' and R", which may be identical or different, each represent hydrogen or hydrocarbyl radicals containing 1 to 30 carbon atoms, and R$^7$ represents an alkylene or phenylene radical.

6. A process according to claim 2, wherein the quaternary ammonium and/or phosphonium cation $Q^+$ is N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, a 1-(2-hydroxyethyl)-3-methylimidazolium cation, 1-(2-carboxyethyl)-3-methylimidazolium cation, diethylpyrazolium, N-butyl-N-methylpyrrolidinium, N-butyl-N-methylmorpholinium, trimethylphenylammonium, tetrabutylphosphonium or tributyl-tetradecylphosphonium.

7. A process according to claim 2, wherein the quaternary sulphonium and quaternary guanidinium cations have the following formulae:

in which $R^1$, $R^2$, $R^3$, $R^4$, $R^5$ and $R^6$, which may be identical or different, are, H, hydrocarbyl radicals containing 1 to 30 carbon atoms or hydrocarbyl radicals carrying one or more —$CO_2R$, —$C(O)R$, —$OR$, —$C(O)NRR'$, —$C(O)N(R)NR'R''$, —$NR'R''$, —$SR$, —$S(O)R$, —$S(O)_2R$, —$SO_3R$, —$CN$, —$N(R)P(O)R'R'$, —$PRR'$, —$P(O)RR'$, —$P(OR)(OR')$, —$P(O)(OR)(OR')$ groups in which R, R' and R", which may be identical or different, each represent hydrogen or hydrocarbyl radicals containing 1 to 30 carbon atoms.

8. A process according to claim 2, wherein the anions $A^-$ are: halides, nitrate, sulphate, alkylsulphates, phosphate, alkylphosphates, acetate, halogenoacetates, tetrafluoroborate, tetrachloroborate, hexafluorophosphate, trifluoro-tris-(pentafluoroethyl)phosphate, hexafluoroantimonate, fluorosulphonate, alkylsulphonates, perfluoroalkylsulphonates, bis(perfluoroalkylsulphonyl)amides, tris-trifluoromethylsulphonyl methylide with formula $C(CF_3SO_2)_3^-$, bis-trifluoromethylsulphonyl methylide with formula $HC(CF_3SO_2)_3^-$, arenesulphonates, arenesulphonates substituted with halogens or halogenalkyl groups, tetraphenylborate anion, tetraphenylborate anions the aromatic rings of which are substituted, tetra-(trifluoroacetoxy)-borate, bis-(oxalato)-borate, dicyanamide, tricyanomethylide, a tetrachloroaluminate anion, or chlorozincate anions.

9. A process according to claim 2, wherein the ionic liquid is 3-butyl-1-methylimidazolium bis(trifluoromethylsulphonyl)amide, 3-butyl-1,2-dimethylimidazolium bis(trifluoromethylsulphonyl)amide, N-butyl-N-methylpyrrolidinium bis(trifluoromethylsulphonyl)amide, 3-butyl-1-methylimidazolium tetrafluoroborate, 3-butyl-1,2-dimethylimidazolium tetrafluoroborate, 3-ethyl-1-methylimidazolium tetrafluoroborate, 3-butyl-1-methylimidazolium hexafluoroantimonate, 3-butyl-1-methylimidazolium trifluoroacetate, 3-ethyl-1-methylimidazolium triflate, 1-(2-hydroxyethyl)-3-methylimidazolium bis(trifluoromethylsulphonyl)amide, 1-(2-carboxyethyl)-3-methylimidazolium bis(trifluoromethylsulphonyl)amide or N-butyl-N-methylmorpholinium bis(trifluoromethylsulphonyl)amide.

10. A process according to claim 1, wherein an unsaturated fat comprising at least one ester formed between at least one monocarboxylic acid comprising at least one ethylenically unsaturated bond and containing at least 12 carbon atoms and at least one aliphatic monoalcohol containing 1 to 8 carbon atoms or glycerol undergoes the metathesis reaction.

11. A process according to claim 10, wherein an unsaturated fat which is oleic sunflower oil or oleic rapeseed oil undergoes the metathesis reaction to produce both an olefinic fraction and a glycerol ester composition at least a portion of chains of which is unsaturated $C_{10}$ chains.

12. A process according to claim 10, wherein an unsaturated fat which is mixtures of monoalcohol esters of oleic sunflower oil or oleic rapeseed oil undergoes the metathesis reaction to produce both an olefinic fraction and a monoalcohol ester composition at least a portion of chains of which is constituted by $C_{10}$ unsaturated chains.

13. A process according to claim 11, wherein the oleic sunflower oil comprises approximately:
oleic acid: about 83% by weight;
linoleic acid: about 10% by weight;
palmitic acid: about 3% by weight;
stearic acid: about 4% by weight.

14. A process according to claim 1, wherein at least one ruthenium compound is used as a catalyst.

15. A process according to claim 14, wherein the catalyst is charged or uncharged catalysts with formula:

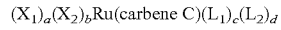

in which:
a, b, c, d are whole numbers in which a and b equal 0, 1 or 2; c and d equal 0, 1, 2, 3 or 4;
$X_1$ and $X_2$, which may be identical or different, each represent a mono- or multi-chelating ligand, charged or uncharged; $X_1$ or $X_2$ may be bonded to $Y_1$ or $Y_2$ or to (carbene C) to form a bidentate ligand on the ruthenium; and
$L_1$ and $L_2$, which may be identical or different, are donor electron ligands.

16. A process according to claim 1 wherein a catalyst is introduced in a proportion comprised between 0.001% molar and 10% molar with respect to the unsaturated starting fat.

17. A process according to claim 1, further comprising separating:
an olefinic fraction containing diolefins and mono-olefins;
and a composition of monoalcohol or glycerol esters.

18. An olefinic fraction obtained by a process comprising contacting at least one unsaturated fat comprising at least one ester formed between at least one monocarboxylic acid comprising at least one ethylenically unsaturated bond and at least one aliphatic monoalcohol or at least one aliphatic polyol, under metathesis conditions, with an excess of ethylene in the presence of a catalyst and in the presence of at least one non-aqueous ionic liquid, and separating:
an olefinic fraction containing diolefins and mono-olefins wherein more than half of its chains are unsaturated $C_{10}$ chains;
and a composition of monoalcohol or glycerol esters said fraction comprising at least 80% 1-decene.

19. An olefinic fraction according to claim 18, comprising 1-heptene and 1,4-pentadiene in addition to at least 80% 1-decene.

20. A process according to claim 17, further comprising separating mono-olefins and diolefins from said olefinic fraction by distillation.

* * * * *